United States Patent
Fenkell

(10) Patent No.: US 8,460,218 B2
(45) Date of Patent: Jun. 11, 2013

(54) PATIENT WEIGHT BEARING MONITOR

(76) Inventor: Randall Fenkell, West Bloomfield, MI (US)

( * ) Notice: Subject to any disclaimer, the term of this patent is extended or adjusted under 35 U.S.C. 154(b) by 104 days.

(21) Appl. No.: 12/956,208

(22) Filed: Nov. 30, 2010

(65) Prior Publication Data

US 2011/0130686 A1    Jun. 2, 2011

Related U.S. Application Data

(60) Provisional application No. 61/264,946, filed on Nov. 30, 2009.

(51) Int. Cl.
*A61B 5/00* (2006.01)

(52) U.S. Cl.
USPC .......................................................... 600/592

(58) Field of Classification Search
USPC ..................... 340/573.1; 600/587, 592, 595
See application file for complete search history.

(56) References Cited

U.S. PATENT DOCUMENTS

| | | | |
|---|---|---|---|
| 3,702,999 A | 11/1972 | Gradisar | |
| 3,791,375 A * | 2/1974 | Pfeiffer | ........................ 600/592 |
| 3,974,491 A | 8/1976 | Sipe | |
| 4,745,930 A | 5/1988 | Confer | |
| 5,107,854 A | 4/1992 | Knotts et al. | |
| 5,253,654 A | 10/1993 | Thomas et al. | |
| 5,511,561 A | 4/1996 | Wanderman et al. | |
| 5,619,186 A | 4/1997 | Schmidt et al. | |
| 6,174,294 B1 | 1/2001 | Crabb et al. | |
| 6,273,863 B1 | 8/2001 | Avni et al. | |
| 2006/0282018 A1 | 12/2006 | Balzano | |
| 2007/0112285 A1* | 5/2007 | Dar et al. | ....................... 600/592 |

* cited by examiner

*Primary Examiner* — Max Hindenburg
(74) *Attorney, Agent, or Firm* — Edell, Shapiro & Finnan, LLC

(57) ABSTRACT

A weight sensor includes a pad of electrically insulative material having a through aperture and electrode plates secured to its top and bottom surfaces at least partially covering the aperture. An electrical contactor in the aperture responds to a compressive force applied across the pad thickness to electrically interconnect the electrodes and close a circuit that permits an alarm to be actuated. The sensor is disposed in footwear worn by a patient being rehabilitated from a lower limb surgery or injury. The stiffness/compressibility of the pad determines the applied patient weight or compressive force required to permit the contactor to close the circuit between the electrodes.

11 Claims, 10 Drawing Sheets

FIG.8

PATIENT WEIGHT BEARING MONITOR

CROSS REFERENCE TO RELATED APPLICATION

This application claims priority from U.S. Provisional Patent Application Ser. No. 61/264,946 entitled "Patient Weight Bearing Monitor" filed Nov. 30, 2009. The disclosure of this provisional patent application is incorporated herein by reference in its entirety.

FIELD OF THE INVENTION

The present invention relates generally to a weight bearing monitor system for recuperating orthopedic patients and, more particularly, to a lower limb load monitoring device for measuring or detecting the amount of force applied to, or weight borne by, a lower limb or joint of the body (either natural or prosthetic) and providing a signal to the user when a predetermined weight threshold level is exceeded.

BACKGROUND

Numerous situations exist where it is important to limit the load or force applied to or borne by a lower natural or prosthetic limb or joint of the body during standing, walking, stepping, running or jumping activities or during rehabilitation therapy. Situations also exist where it is important that the lower limb or joint be exposed to a certain load or force, particularly during rehabilitation therapy. In both situations it is important to monitor such load or force and to provide a signal to the user when such force is exceeded or met. Examples include post-surgery or injury rehabilitation of hips, knees, ankles or any other portion of the body which is affected by force applied to or borne by at least one of the user's legs, or any other situation in which monitoring of the weight on a lower limb during standing, walking, jumping or other activities is desired.

Prior art systems for monitoring the load or force applied to joints in a patient's leg are found in U.S. Patent Application Pub. No. 2006/0282018 and in the following U.S. Pat. Nos. 3,702,999 (Gradisar); 3,791,375 (Pfeiffer); 3,974,491 (Sipe); 4,745,930 (Confer); 5,107,854 (Knotts et al); 5,253,654 (Thomas et al); 5,511,561 (Wanderman et al); 5,619,186 (Schmidt et al); 6,174,294 (Crabb et al); and 6,273,863 (Avni et al).

Prior art monitors are typically complex mechanically and/or electrically with the result that they are expensive and add significantly to a patient's cost of recuperation.

SUMMARY OF THE INVENTION

The present invention provides an inexpensive alternative to methods and apparatus utilized heretofore to monitor the load applied to a lower limb or joint by a patient's weight and to provide an alarm when a predetermined and selectable weight is applied or exceeded.

A sensor according to the present invention includes a pad of electrically insulative material, having top and bottom surfaces defining its thickness dimension, and provided with a through aperture communicating between those surfaces. First and second thin electrically conductive plates or sheets serve as electrodes and are secured to the top and bottom surfaces of the pad, covering or partially covering the ends of the aperture. A resilient electrical contactor secured to the underside of the top plate depends through a portion of the aperture toward the bottom plate. The resulting structure serves as an electrical switch that is normally open but closes when the compressive force applied across the pad thickness is sufficient to permit the contactor to contact the bottom plate through the pad aperture. Electrical lead wires secured to respective electrodes are connected to a circuit that permits an audible and/or visible alarm to be actuated when the switch is closed.

The pad is typically disposed between the sole of a patient's foot and the ground, preferably in a patient's sock, shoe or other footwear or foot-worn orthopedic structure. The stiffness or compressibility of the pad determines the applied weight or compressive force required to permit the contactor to close the circuit between the electrodes, resulting in the closure of the switch. By selecting pad material having appropriate compressibility characteristics, one can design the switch to close in response to different applied forces. Patients can use sensors of increasing stiffness as rehabilitation progresses and greater weight loads are permitted on the affected limb.

The above and still further features and advantages of the present invention will become apparent upon consideration of the following definitions, descriptions and descriptive figures of specific embodiments thereof wherein like reference numerals in the various figures are utilized to designate like components. While these descriptions go into specific details of the invention, it should be understood that variations may and do exist and would be apparent to those skilled in the art based on the descriptions herein.

DESCRIPTION OF THE PREFERRED EMBODIMENTS

Figure 1:
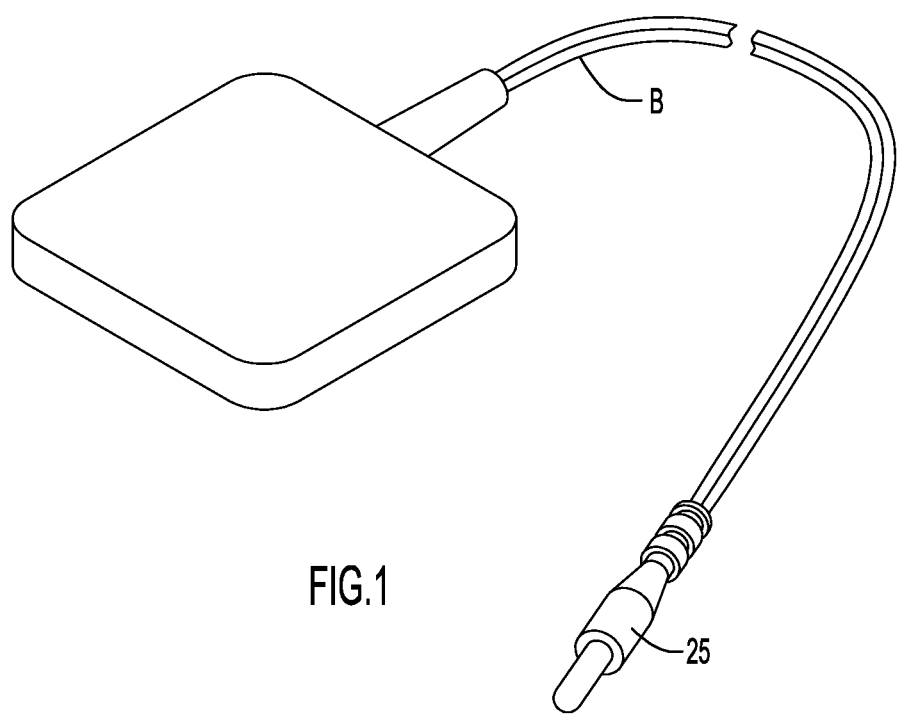
FIG. 1 is a view in perspective of the sensor portion of a weight monitor assembly according to the present invention.

The following detailed explanations of the preferred embodiments reveal the methods and apparatus of the present invention.

Referring to FIGS. 1 through 7, a weight sensor 17 comprises an electrically non-conductive pad 10, preferably made of silicone or like material and typically approximately 0.25" thick, is shown in a rectangular configuration with top and bottom surfaces and a centrally located aperture 13 defined through its thickness. Neither the pad 10 nor the aperture 13 is required to be rectangular and can be any shape, such as round, polygonal, irregular, etc., as may be consistent with the functional features described herein. Top and bottom electrically conductive electrode sheets or plates 11 and 12, respectively, are disposed on respective top and bottom surfaces of pad 10 to partially or fully cover opposite ends of aperture 13. In the illustrated embodiment sheets 11 and 12 have the same peripheral configuration, in this case rectangular, as pad 10 and overlie the entireties of respective top and bottom surfaces of the pad. A resiliently movable electrical contactor 15, preferably made of resiliently bendable spring steel, is secured by soldering or other electrical connection to the underside of top plate 11. Contactor 15 includes a short section extending along the underside of plate 11 and a bent section extending at an angle (e.g., 45°) into aperture 13. It is to be understood that an angular configuration of contactor 15, and the particular angle of 45°, are design choices, and that any electrically conductive contactor configuration that permits the contactor to move toward the opposing electrode plate under weight loading may be employed.

Figure 2:
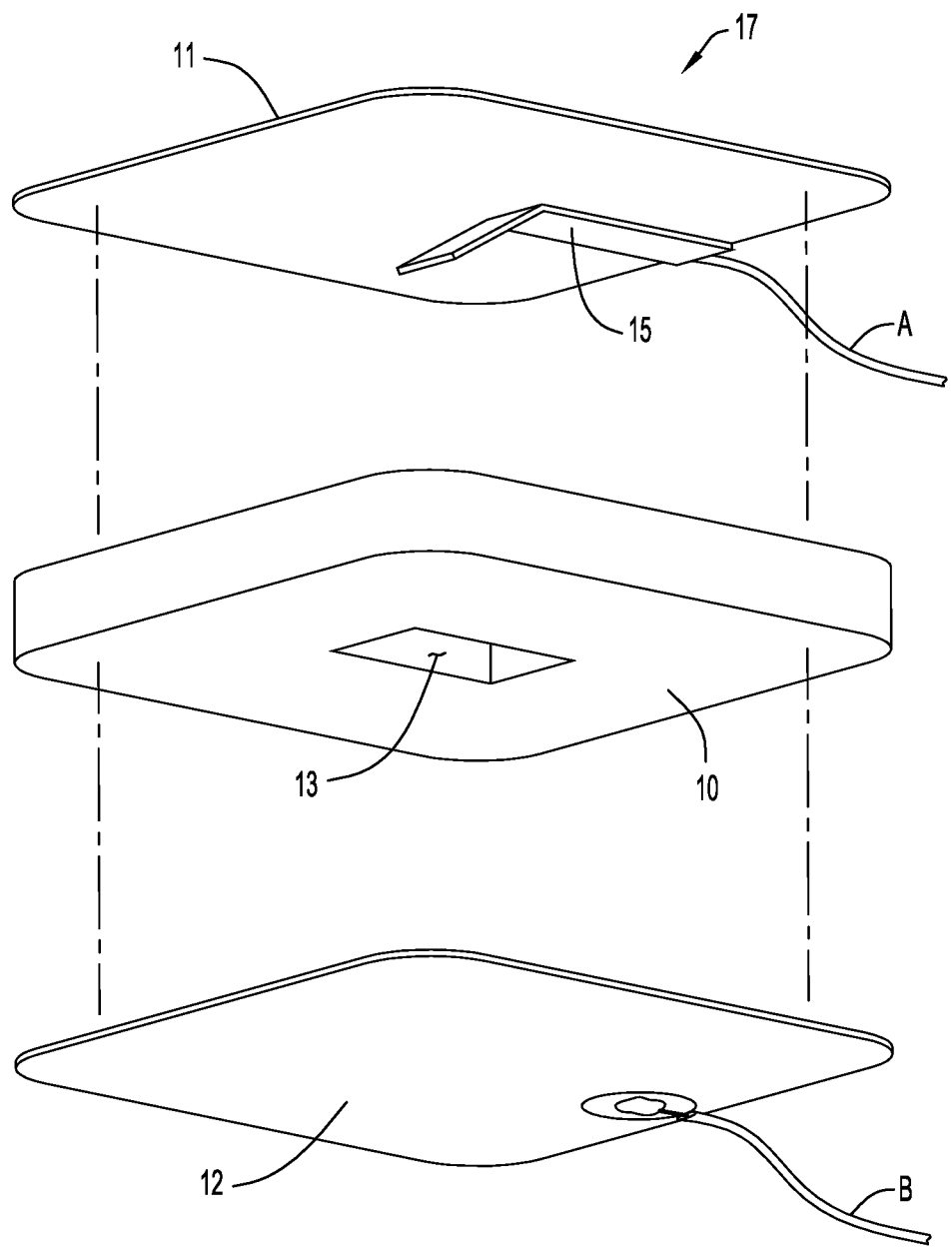
FIG. 2 is an exploded view in perspective of a sensor unit employed in the assembly of FIG. 1.
Figure 3:
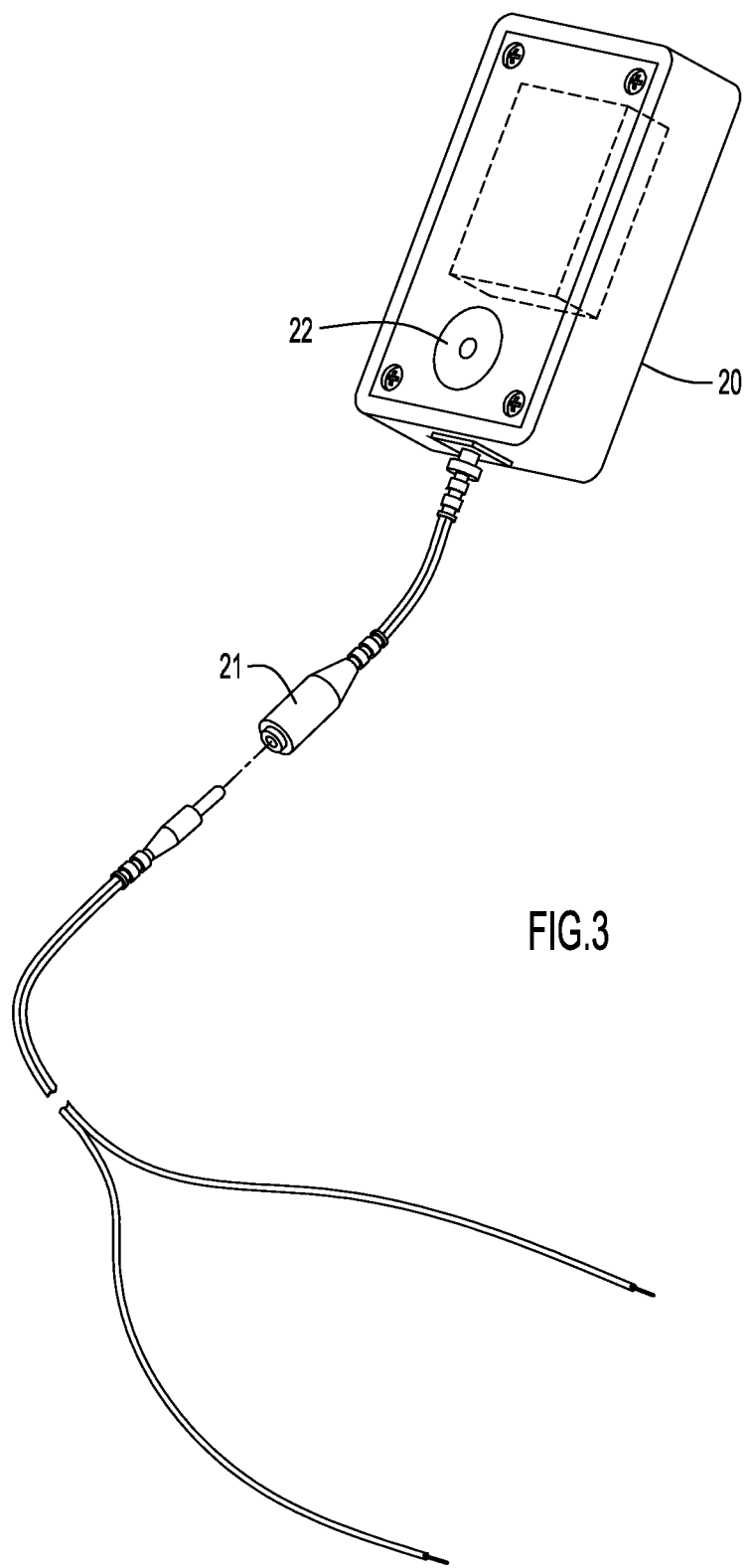
FIG. 3 is a view in perspective of one form of an indicator portion of the weight monitor assembly of the present invention.

In the illustrated preferred embodiment each electrode sheet 11, 12 is made of steel and is approximately 0.020" thick, although other conductive materials (e.g., copper, aluminum) may be employed. Electrically conductive wire leads A and B are connected, by soldering or the like, to respective electrode sheets 11 and 12. As illustrated in FIG. 2, the opposite ends of wire leads A and B are connected to a plug 25 which is adapted to connect to respective terminals in a control box receptacle or jack 21. The control box 20 contains a buzzer 22, or other audible or visual alarm, and a voltage source such as a battery 28 (or batteries) connected in series between the terminals of jack 21. Thus, when there is contact between electrode plates 11 and 12 by means of contactor 15 being forced further through aperture 13, a circuit is closed across the batteries and alarm 22 as best illustrated in the schematic diagram of FIG. 7. Such contact is made when the force applied across weight sensor unit 17 is sufficient to compress pad 10 to cause contactor 15 to contact bottom plate 12 and resiliently bend so that the circuit between plates 11 and 12 is closed. That force is the weight of a patient applied across the unit by the sole of a patient's foot urging the unit toward a floor or the ground through a sock, shoe or other footwear in which the sensor is located. It will be appreciated that contactor 15 may be secured instead to the bottom plate 12 and positioned to be forced into contact with top plate 11 when the pressure applied across the unit is sufficient to compress pad 10 to cause contactor 15 to contact top plate 12 and resiliently bend so that the circuit between plates is closed. In either case the resilience of the contactor permits the predetermined force to be exceeded without damaging the contactor.

Figure 4:
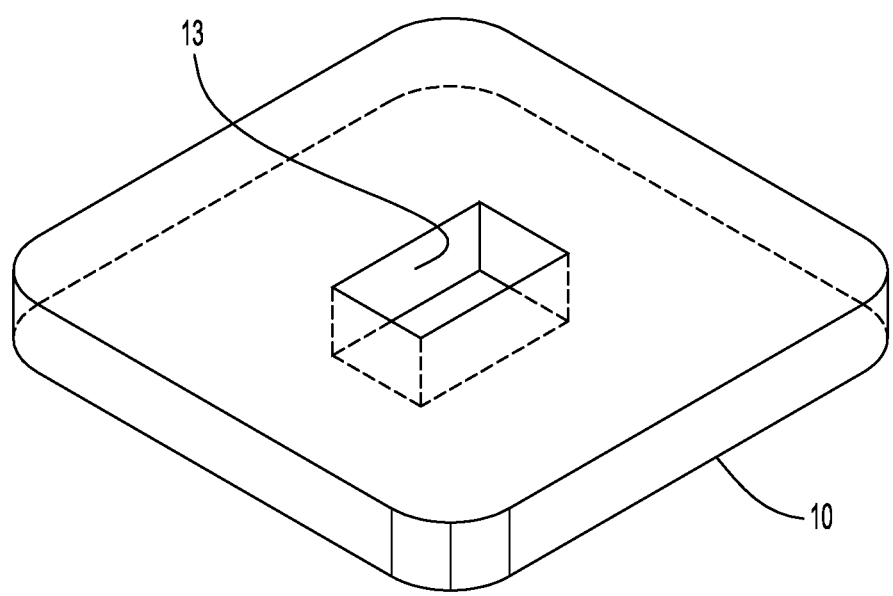
FIG. 4 is a view in perspective of a compressible pad employed in the sensor unit of FIG. 2.
Figure 5:
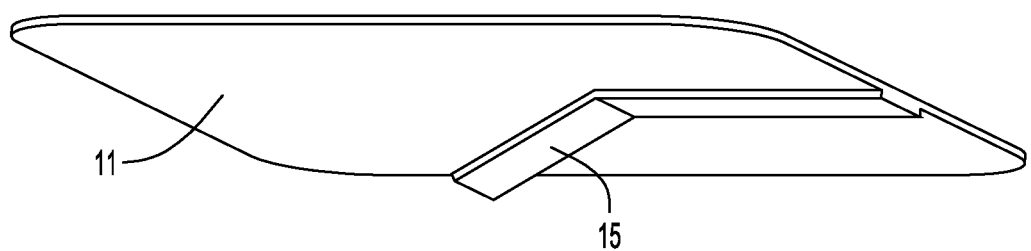
FIG. 5 is a view in perspective of one form of an electrode and contactor employed in the sensor unit of FIG. 2.

As best illustrated in FIG. 4, pad 10 may be a two inch square of molded silicone with a density selected to permit compression of the pad to effect contact between the electrode sheets in response to application of a predetermined force across the pad. Pads of different densities can be provided to permit different applied weights to actuate the alarm as a patient's rehabilitation progresses; that is, differently calibrated sensors can be provided to sound an alarm at different applied weights.

As illustrated in FIG. 2, the electrode plates may be substantially identical except for the provision of contactor 15 on the underside of plate 11. The wire leads A and B are preferably 22 gauge wire. As noted elsewhere herein, the electrodes need not be identical, and only one electrode is required to flex to permit contactor movement as the pad 10 is compressed under a weight load.

Figure 6:
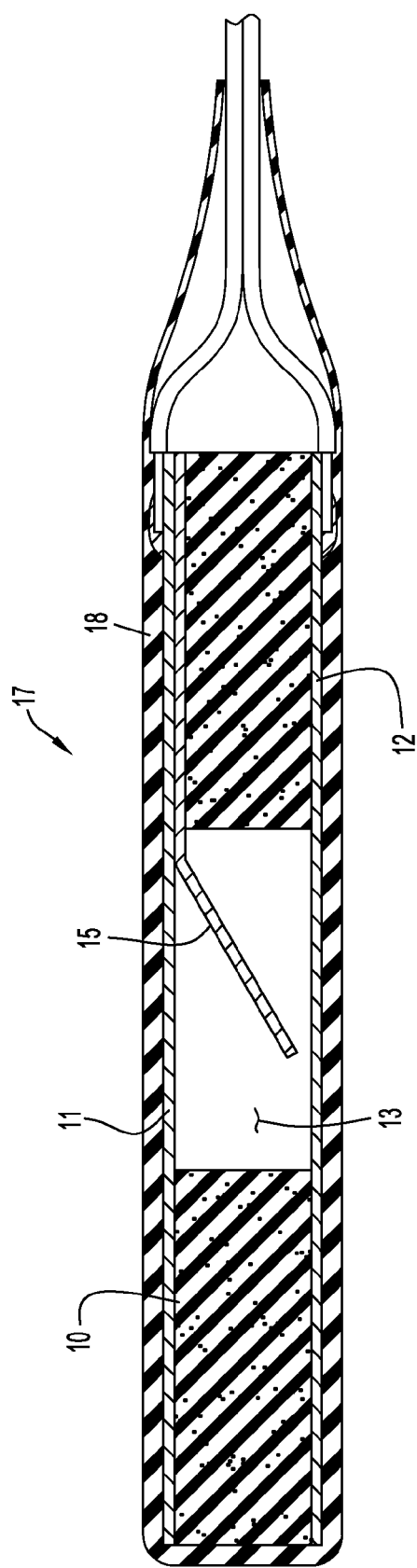
FIG. 6 is a view an elevation view in section of the sensor of FIG. 2.

Referring to FIG. 6, the sensor unit may be encased in an electrically insulative sleeve 18 that can be placed in footwear such as a sock, shoe or orthopedic appliance when used by a patient. Sleeve 18 may be made of cotton, polyester or any such deformable material that serves as a cover for the unit and does not interfere with its operation. Alternatively, sleeve 18 may be encapsulated about the sensor unit by dipping the sensor in molten encapsulation material (e.g., a rubber like compound) or brushing on the compound. That compound may be color coded to indicate the compression weight at which electrical contact is made between the electrodes of the unit. As assembled, the unit 17 typically weighs two pounds or less.

Figure 7:
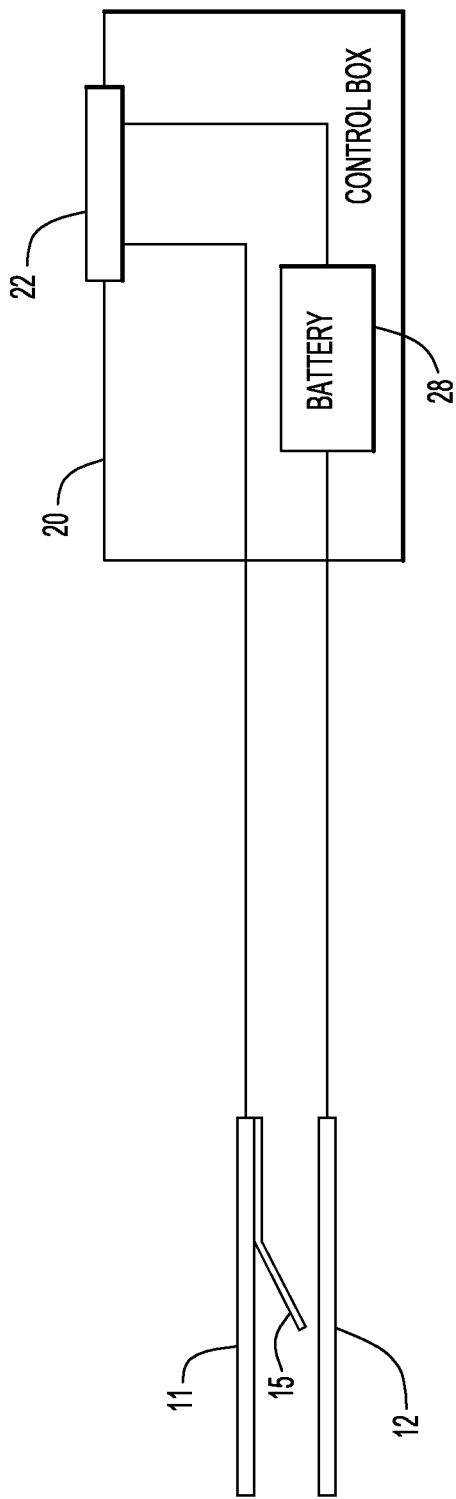
FIG. 7 is an electrical schematic diagram of the weight monitor of the present invention.
Figure 8:
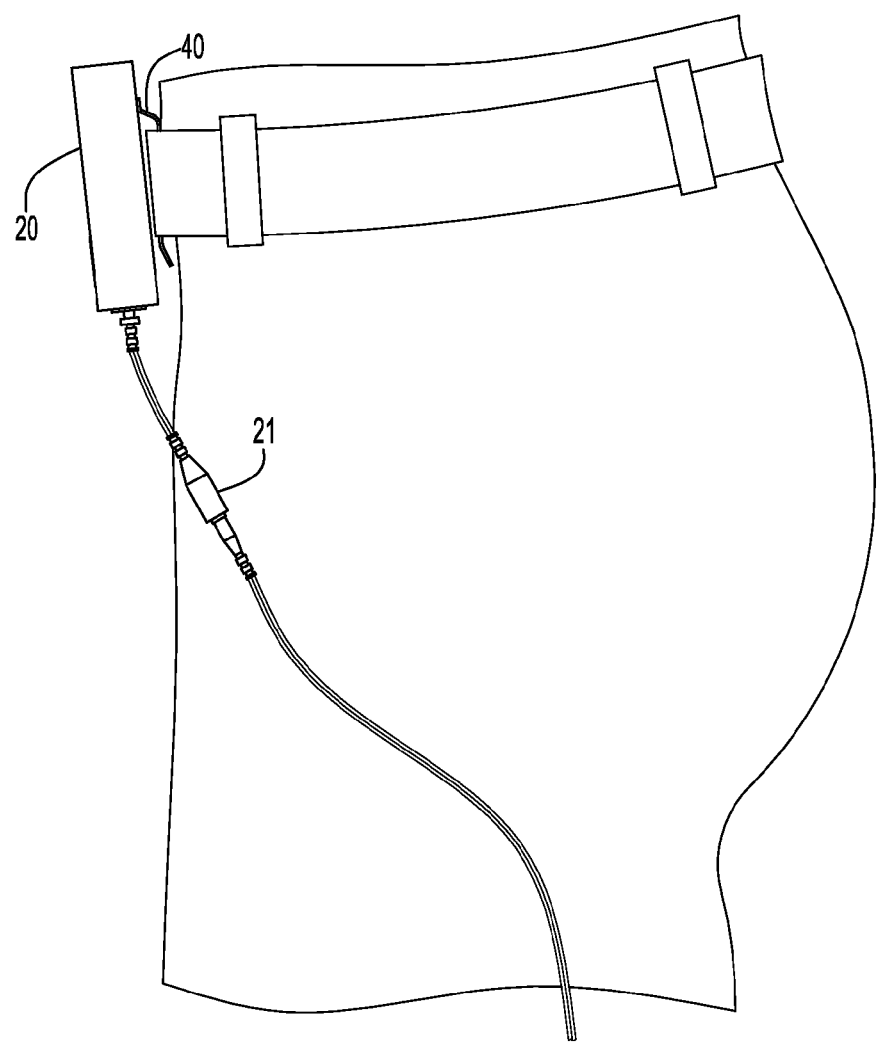
FIG. 8 is a broken view in elevation showing the weight monitor assembly of the present invention deployed on a patient with the sensor located in the patient's shoe.
Figure 8:
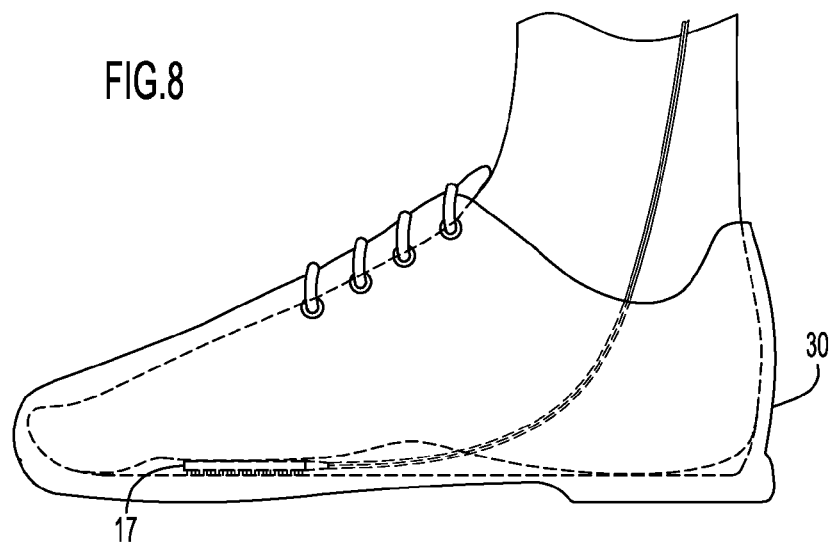

The weight sensor of the present invention may be used in several ways. One such way is illustrated in FIG. 8 wherein the sensor unit 17 is shown removably secured, by means of hook and loop fastener, or the like, to the interior sole of a patent's shoe 30. The sole of the patient's foot applies the patient's weight to the top plate 11 (FIG. 1) of the sensor, thereby compressing the sensor pad 10 and gradually moving the contactor 15 toward the bottom plate 12. When the maximum permitted weight is applied across the sensor, contactor 15 contacts the bottom plate, closing the circuit and sounding or flashing an alarm at the control box 20 (FIG. 7). The control box may be connected by means of a clip 40, or the like, to the top of a sock or a belt, etc., worn by the patient.

Figure 9:
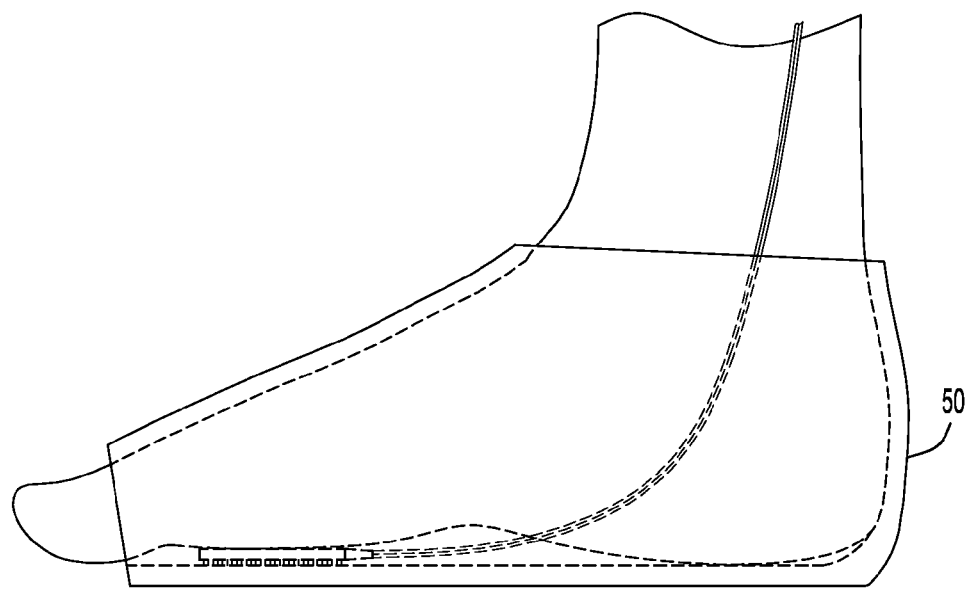
FIG. 9 is a view in elevation showing the sensor of the weight monitor assembly located in an orthopedic appliance worn by the patient during rehabilitation therapy.

An alternative manner of using the weight sensor is illustrated in FIG. 9 wherein an orthopedic appliance 50 or similar structure is shown being worn on a patient's foot. The sensor is removably secured to the interior sole of the appliance.

Figure 10:
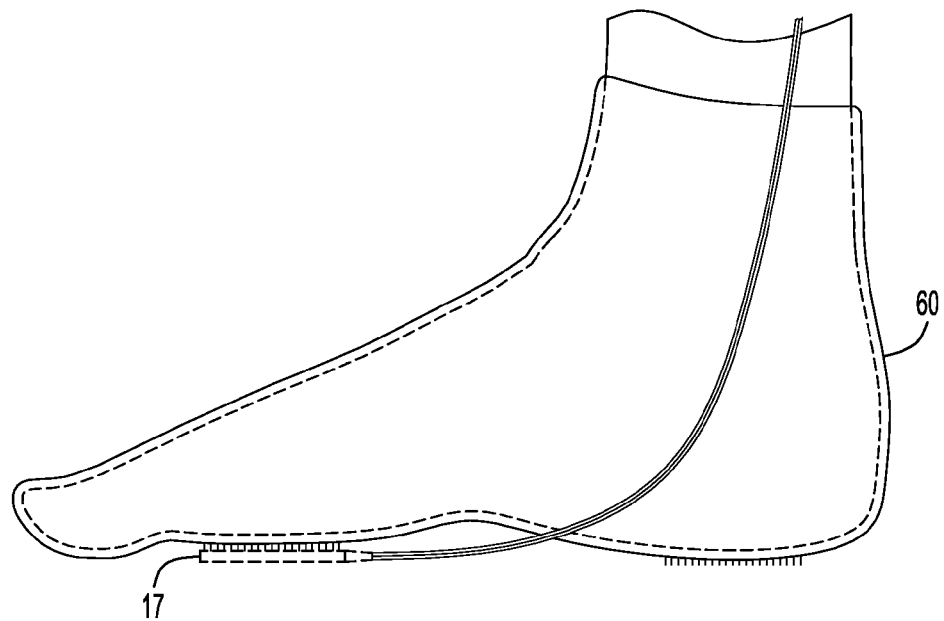
FIG. 10 is a view in elevation showing the sensor of the weight monitor assembly attached by a hook and loop fastener to a sock worn by the patient during rehabilitation therapy.
Figure 11:
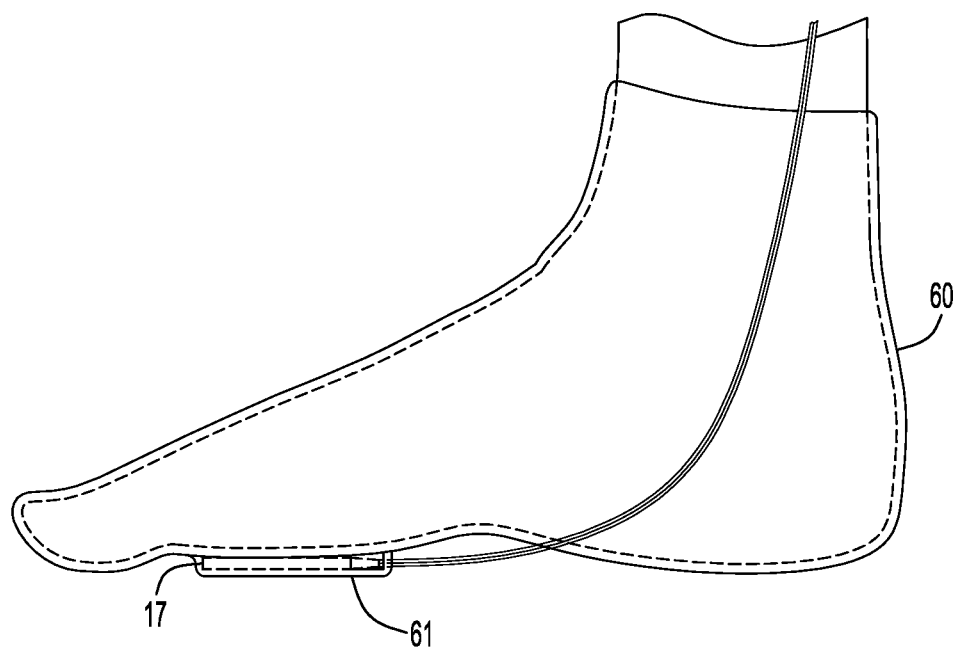
FIG. 11 is a view in elevation showing the sensor of the weight monitor assembly inserted in a pocket of a sock worn by the patient during rehabilitation therapy.

In another embodiment the sensor is removably secured to the bottom of a patient's sock 60, as illustrated in FIG. 10. Alternatively, as shown in FIG. 11, the sock 60 may be provided with a pocket 61 on the bottom side of the sock sole to receive the sensor. The lead wires connect to the control box which may be attached to the pants or other garment worn by the patient.

The foregoing describes only a few of the many ways in which the sensor 17 may be deployed for use.

The dimensions described herein for the preferred embodiments are presented simply as examples and can vary as desired in order to provide a suitably functional and comfortable unit. For example, the pad 10 need not be square; instead it can be round, oval, rectangular, contoured to a portion of the patient's foot, or irregular in shape. The pad length and/or width can be adjusted as desired, although it is believed that 1.5" and 3.0" are practical limits on these dimensions. The thickness of the pad 10 can range from 0.100" to 0.400".

The material for the pad 10 is chosen to provide a desired compression versus applied weight characteristic and can be solid/dense and sponge-like material including neoprene, silicone, natural rubber, latex, buna N, buna S, hypalon, EPDM, or polyurethane. The pad can be cut from sheet material, using a steel ruler die, shearing or cutting by hand. The material can also be molded to the needed shape.

Aperture 13 can be square, rectangular, round or any convenient regular or irregular shape and can have any length and width dimensions appropriate to the described function. Examples would be in the range of 0.250" to 1.000".

The top and bottom plates 11, 12 can be conductive steel or aluminum, or they can be plastic with attached metal strips to provide the desired electrical conductivity. The thickness of the plates may, for example, range from 0.015" to 0.125". Importantly, in the illustrated embodiment the plates must be sufficiently thin to resiliently flex and follow the pad surfaces to which they are attached under a weight load. It will be appreciated that only one of the plates is required to flex as the pad compresses and, therefore, the plates need not be identical in structure or function.

In order for electrical contact to be made between electrodes 11 and 12 by contactor 15, pad 10 is typically required to be compressed by approximately 50%, depending on the configuration, dimensions and positioning of the contactor. This compression is effected at different applied weights, typically between 5 and 40 lbs., depending on the compression characteristics of the pad which are predetermined by blending various compounds and then testing for the compression needed.

It will be appreciated that the important feature of unit is that, as pad 10 is compressed under the load of a patient's weight applied across the pad thickness dimension, contact will ultimately be made between electrodes 11 and 12 when a predetermined load force is reached. The use of contactor 15 attached to one of the electrodes and functioning through an aperture 10 is only one way of establishing this contact. For example, an electrically conductive member may be partially embedded in pad 10 in spaced relation to one or both electrodes and positioned to make contact between the electrodes through a recess or other opening in a pad surface in response to a predetermined pad compression.

Contactor 15 can be made of a strip of spring steel, or a small spring. As an alternative to the single contactor, the top and bottom plates can be provided with a lip, each facing the other, so that lips can be used to make the electrical contact upon compression of the pad.

The lead wires can be as short as a few inches and as long as necessary to reach the control box from the sensor, depending on where the control box is to be worn. The control box can be made of metal or plastic and can have any suitable size and shape to house the indicated components.

The battery voltage may be between 1.5 volts to 9 volts. A buzzer or other alarm that is operative with the chosen voltage supplies a sound or flashing light to alert the user that that he has reached the critical weight set by the physician or therapist. That is, the unit is used to indicate to the patient that the weight being applied to the limb is at the maximum weight that the person conducting the therapy has indicated to be appropriate. Sensor units can be made to respond to a large number of different weights needed by the medical profession.

The sensor of the present invention prevents patients who are undergoing therapy for an injured limb or replaced joint from suffering damage caused by placing more weight on the limb or joint than can be safely applied at different stages of recovery. A primary advantage of the sensor of the present invention is that can be manufactured and sold for a price that is far less than other sensors currently being used for the same purpose, thereby allowing patients to purchase the unit.

As described and illustrated, the sensor can be used attached to a stocking, placed in a shoe or sandal, or attached to a form fitting appliance.

Having described preferred embodiments of new and improved weight bearing monitor system, it is believed that other modifications, variations and changes will be suggested to those skilled in the art in view of the teachings set forth herein. It is therefore to be understood that all such variations, modifications and changes are believed to fall within the scope of the present invention as defined by the appended claims. Although specific terms are employed herein, they are used in a generic and descriptive sense only and not for purposes of limitation.

What is claimed is:

1. A method of actuating an alarm when the weight of a patient applied on a lower limb of the patient exceeds predetermined weights, said method comprising the steps of:
    (a) providing a first sensor as a first electrically insulative compressible pad between two first pad electrodes that are spaced across the thickness of the first pad, the first pad being comprised of a material having a first density;
    (b) selecting said first density to calibrate the first sensor such that, in response to application of a force exceeding a first predetermined force across the first pad thickness, compression of the first pad effects electrical contact between the two first pad electrodes;
    (c) providing at least a second sensor as a second electrically insulative compressible pad between two second pad electrodes that are spaced across the thickness of the second pad, the second pad being comprised of a material having a second density;
    (d) selecting said second density different from said first density to calibrate the second sensor such that, in response to application of a force exceeding a second predetermined force across the second pad thickness, compression of the second pad effects electrical contact between the two second pad electrodes, wherein said second predetermined force is different from said first predetermined force;
    (e) alternatively positioning said first and second sensors beneath the foot of the patient to enable weight of the patient to be applied through the lower limb across the sensor thickness;
    (f) providing an electrical signal in response to electrical contact between the two first pad electrodes and in response to electrical contact between the two second pad electrodes; and
    (g) actuating said alarm with said electrical signal.

2. The method of claim 1 wherein step (b) includes:
    (b.1) providing a first pad aperture extending through the entire thickness of said first pad; and
    (b.2) securing a first pad electrical contactor to one of said first pad electrodes and extending through said aperture toward the other of said first pad electrodes, said first pad contactor being positioned to be spaced from said other of said first pad electrodes in the absence of force applied across the first pad thickness and in contact with said other of said first pad electrodes in response to application of a force exceeding said first predetermined force across the first pad thickness;
    and wherein step (d) includes:
    (d.1) providing a second pad aperture extending through the entire thickness of said second pad; and
    (d.2) securing a second pad electrical contactor to one of said second pad electrodes and extending through said second pad aperture toward the other of said second pad electrodes, said contactor being positioned to be spaced from said other of said second pad electrodes in the absence of force applied across the second pad thickness and in contact with said other of said second pad electrodes in response to application of a force exceeding said second predetermined force across the first pad thickness.

3. The method of claim 2 further comprising providing said first pad electrical contactor and said second pad electrical contactor as respective resiliently bendable and electrically conductive metal members.

4. The method of claim 1 wherein step (e) includes disposing one of said first and second sensors in an article of footwear in a position to be stepped upon when the article is worn.

5. The method of claim 1 wherein step (e) includes disposing one of said first and second sensors in a sock in a position to be stepped upon when the article is worn.

6. The method of claim 1 wherein step (e) includes disposing one of said first and second sensors in a shoe in a position to be stepped upon when the article is worn.

7. A method of actuating an alarm when the weight of a patient applied on a lower limb of the patient exceeds predetermined weights, said method comprising the steps of:
(a) providing a first sensor as a first electrically insulative compressible pad between two first pad electrodes that are spaced across the thickness of the first pad, the first pad being comprised of a material having a first compression versus applied weight characteristic determining the amount of pad thickness compression that results from a patient's applied weight across the thickness of the first pad;
(b) selecting said first characteristic to calibrate said first sensor such that, in response to application of a force exceeding a first predetermined force across the first pad thickness, compression of the first pad effects electrical contact between the two first pad electrodes;
(c) providing at least a second sensor as a second electrically insulative compressible pad between two second pad electrodes that are spaced across the thickness of the second pad, the second pad being comprised of a material having a second compression versus applied weight characteristic determining the amount of pad thickness compression that results from a patient's applied weight across the thickness of the second pad;
(d) selecting said second characteristic different from said first characteristic to calibrate said second sensor such that, in response to application of a force exceeding a second predetermined force across the second pad thickness, compression of the second pad effects electrical contact between the two second pad electrodes, wherein said second predetermined force is different from said first predetermined force;
(e) alternatively positioning said first and second sensors beneath the foot of the patient to enable weight of the patient to be applied through the lower limb across the sensor thickness;
(f) providing an electrical signal in response to electrical contact between the two first pad electrodes and in response to electrical contact between the two second pad electrodes; and
(g) actuating said alarm with said electrical signal.

8. The method of claim 7 wherein step (b) includes:
(b.1) providing a first pad aperture extending through the entire thickness of said first pad; and
(b.2) securing a first pad electrical contactor to one of said first pad electrodes and extending through said aperture toward the other of said first pad electrodes, said first pad contactor being positioned to be spaced from said other of said first pad electrodes in the absence of force applied across the first pad thickness and in contact with said other of said first pad electrodes in response to application of a force exceeding said first predetermined force across the first pad thickness;
and wherein step (d) includes:
(d.1) providing a second pad aperture extending through the entire thickness of said second pad; and
(d.2) securing a second pad electrical contactor to one of said second pad electrodes and extending through said second pad aperture toward the other of said second pad electrodes, said contactor being positioned to be spaced from said other of said second pad electrodes in the absence of force applied across the second pad thickness and in contact with said other of said second pad electrodes in response to application of a force exceeding said second predetermined force across the first pad thickness.

9. The method of claim 8 further comprising providing said first pad electrical contactor and said second pad electrical contactor as respective resiliently bendable and electrically conductive metal members.

10. A method of actuating an alarm when a patient's weight applied on a lower limb of the patient exceeds predetermined weights, said method comprising the steps of:
(a) positioning a sensor beneath the foot of the patient to enable the weight of the patient to be applied through the lower limb across the sensor thickness when the patient stands on the foot, wherein step (a) includes:
(a.1) providing the sensor as a first electrically insulative compressible pad between two electrodes spaced across the thickness of the first pad, and calibrating the first pad by providing the first pad with a first compression versus applied weight characteristic determining the amount of pad thickness compression that results from a patient's applied weight across the thickness of the first pad;
(a.2) making electrical contact between the two electrodes in response to the applied weight across the thickness of the first pad exceeding a first threshold weight;
(a.3) replacing the first pad with at least a second electrically insulative compressible pad between two electrodes spaced across the thickness of the second pad, and calibrating the second pad by providing the second pad with a second compression versus applied weight characteristic determining the amount of pad thickness compression that results from a patient's applied weight applied the thickness of the second pad, wherein the second characteristic is different from the first characteristic;
(a.4) making electrical contact between the two electrodes in response to the weight applied across the thickness of the second pad exceeding a second threshold weight different from said first threshold weight;
(b) providing an electrical signal in response to electrical contact between the two electrodes; and
(c) actuating said alarm with said electrical signal.

11. The method of claim 10 further comprising providing said first pad electrical contactor and said second pad electrical contactor as respective resiliently bendable and electrically conductive metal members.

* * * * *